(12) United States Patent  
Duvoisin

(10) Patent No.: US 10,143,222 B2  
(45) Date of Patent: Dec. 4, 2018

(54) COMPACT DEVICE FOR ELECTROLYTIC STERILIZATION OF FOOD AND UTENSILS

(71) Applicant: Charles Adriano Duvoisin, São Bento do Sul (BR)

(72) Inventor: Charles Adriano Duvoisin, São Bento do Sul (BR)

( * ) Notice: Subject to any disclaimer, the term of this patent is extended or adjusted under 35 U.S.C. 154(b) by 205 days.

(21) Appl. No.: 14/900,811

(22) PCT Filed: Jun. 20, 2014

(86) PCT No.: PCT/BR2014/000198  
§ 371 (c)(1),  
(2) Date: Dec. 22, 2015

(87) PCT Pub. No.: WO2015/000045  
PCT Pub. Date: Jan. 8, 2015

(65) Prior Publication Data  
US 2016/0135492 A1    May 19, 2016

(30) Foreign Application Priority Data

Jul. 5, 2013   (BR) .............................. 102013017403

(51) Int. Cl.  
*A23L 3/32*     (2006.01)  
*A61L 2/03*     (2006.01)

(52) U.S. Cl.  
CPC ............. *A23L 3/325* (2013.01); *A61L 2/035* (2013.01); *A61L 2202/11* (2013.01); *A61L 2202/16* (2013.01); *Y02E 60/366* (2013.01)

(58) Field of Classification Search  
CPC .......... A47J 27/0802; A23L 3/32; A23L 3/325  
See application file for complete search history.

(56) References Cited

U.S. PATENT DOCUMENTS 3,652,430 A * 3/1972 Beck .................. C25B 3/10  
                                                    204/221  
3,854,051 A * 12/1974 Hudson ............... B01J 19/088  
                                                    422/186.04

(Continued)

FOREIGN PATENT DOCUMENTS

CN        201312728 Y   *  9/2009  
GB        2487796 A       8/2012

(Continued)

OTHER PUBLICATIONS

Presto Electric Skillet with Glass Cover, obtained at https://www.gopresto.com/downloads/instructions/06852.pdf on Oct. 13, 2017, 2011 (no month available), pp. 1-4 (Year: 2011).*

(Continued)

*Primary Examiner* — Harry D Wilkins, III  
(74) *Attorney, Agent, or Firm* — Knobbe, Martens, Olson & Bear LLP

(57) ABSTRACT

The present invention refers to a compact device for electrolytic sterilization of food and utensils, especially for the electrical treatment of food and utensils using the electric current generated between a positive pole and a negative pole of an electrolysis system, all of those immersed in a fluid medium contained within a container covered by a lid of said device. The container is the anode or positive pole and the lid, by means of a cathode shaft provided with a cathode disc, is the cathode or negative pole, and the electrolyte is water.

8 Claims, 5 Drawing Sheets

(56) References Cited

U.S. PATENT DOCUMENTS

| | | | | |
|---|---|---|---|---|
| 3,941,666 A * | 3/1976 | Mitzlaff | ............... | C25B 3/00 |
| | | | | 205/434 |
| 3,941,669 A * | 3/1976 | Bharucha | ............... | C25B 9/162 |
| | | | | 204/222 |
| 4,002,552 A * | 1/1977 | Bunn, Jr. | ............... | C25B 15/02 |
| | | | | 204/228.2 |
| 4,177,116 A * | 12/1979 | DeNora | ............... | C25B 9/168 |
| | | | | 204/252 |
| 4,522,834 A * | 6/1985 | Miyahara | ............... | A23L 3/005 |
| | | | | 219/771 |
| 6,348,143 B1 * | 2/2002 | Serikawa | ............... | B01J 3/04 |
| | | | | 204/242 |
| 6,585,882 B1 * | 7/2003 | Su | ............... | B01D 53/32 |
| | | | | 204/242 |
| 6,949,721 B2 * | 9/2005 | Simic-Glavaski | ...... | A47J 27/00 |
| | | | | 219/386 |
| 7,857,952 B2 * | 12/2010 | Yoshida | ............... | B08B 3/14 |
| | | | | 118/429 |
| 2006/0113186 A1 * | 6/2006 | Hodgson | ............... | C25B 1/245 |
| | | | | 204/297.01 |
| 2006/0137973 A1 * | 6/2006 | Herrington | ............ | A61L 2/035 |
| | | | | 204/196.06 |

FOREIGN PATENT DOCUMENTS

| | | | |
|---|---|---|---|
| JP | 06-253755 A | * | 9/1994 |
| JP | H11 215974 A | | 8/1999 |
| JP | 2002/153248 A | | 5/2002 |
| JP | 3221136 B2 | | 10/2011 |
| WO | WO 2006/058282 A2 | | 6/2006 |
| WO | WO 2010-030039 A | | 3/2010 |

OTHER PUBLICATIONS

Paeilleux et al. Lethal Effects of Electric Current on *Escherichia coli*, Applied Microbiology, vol. 19, No. 3, Mar. 1970, pp. 421-424 (Year: 1970).*

Park et al, Inactivation of Bacteria in Seawater by Low-Amperage Electric Current, Applied and Environmental Microbiology, vol. 69, No. 4, Apr. 2003, pp. 2405-2408 (Year: 2003).*

Machine translation of JP 06-253755, obtained from http://worldwide.espacenet.com on Apr. 24, 2018 (Year: 1994).*

International Search Report and Written Opinion dated Aug. 26, 2014 in PCT Application No. PCT/BR2014/000198.

Davis et al., Effects of Microamperage, Medium, and Bacterial Concentration on Iontophoretic Killing of Bacteria in Fluid, Antimicrobial Agents and Chemotherapy, Apr. 1989, pp. 442-447, vol. 33, No. 4.

Extended European Search Reported dated Jan. 30, 2017, received in European Patent Application No. EP 14819771.8; 6 pages.

Liu et al., Mechanisms of the Bactericidal Activity of Low Amperage Electric Current (DC), Journal of Antimicrobial Chemotherapy, (1997), pp. 687-695, 39.

Park et al., Inactivation of Bacteria in Seawater by Low-Amperage Electric Current, Applied Environmental Microbiology, Apr. 2003, pp. 2405-2408, 69(4).

* cited by examiner

COMPACT DEVICE FOR ELECTROLYTIC STERILIZATION OF FOOD AND UTENSILS

FIELD OF APPLICATION

The present invention relates to the field of sterilization and/or disinfection of food and utensils by electrolysis.

Introduction

The present invention refers to a compact device for electrolytic sterilization of food and utensils, wherein said device is provided with a main container and with a lid which represent, respectively, the positive pole (anode) and the negative pole (cathode) of an electrolytic system powered by alternating current, directly connected to the two-phase electrical grids of homes, industrial kitchens, small food industries, nursing homes, hospitals, emergency rooms, veterinary clinics, pet shops and the like.

TECHNICAL BACKGROUND

The state of the art found to be pertinent to the object of the present invention discloses different solutions for sterilizing food and/or utensils.

German Patent DE 10 2009 016 821 discloses a device (1) for electrically treating foods (2), at least comprising a liquid tank (3), which can accommodate a cleaning liquid (4), a direct-current supply (5), two electrodes (9a, 9b), and a liquid drain (6), by means of which the exiting cleaning liquid (4) can be conducted directly to the food (2) to be treated and/or can be temporarily stored in a buffer tank. Said patent document also discloses that food (2) to be treated is in direct electrical contact with the cleaning liquid (4). The fact that DE 10 2009 016 821 provides the conveyance of the cleaning liquid (4) directly to the food (2) or its temporary storage in a buffer tank for the subsequent immersion of food (2) to be treated, limits its application to larger volume conditions of the element to be treated, and the actual amount of the element under consideration. Furthermore, said power supplying is of direct current type, which requires the use of specific electric power sources.

The Brazilian utility model patent application No. MU8700282-5 discloses a device for the generation of active chlorine in the presence of an organic load of sodium chloride in water, wherein a recirculation system for electrochemically activated solutions returns antimicrobial solution which has been depleted of active antimicrobial species to an electrolytic cell (10) for regeneration of the active species. According to the Inventor, the concentration of active species is maintained at a level at which an efficient sterilization is achieved by means of the recirculation of the antimicrobial agent by using the electrolytic cell for regeneration of the active species, However, said patent document MU8700282-5 uses a solution of sodium chloride as its electrolyte. Consequently, this can, for instance, affect the flavour of food to be treated and even promote or accelerate oxidation processes on ferrous metal utensils.

International patent WO 9908719 discloses a sterilization apparatus utilizing catholyte and anolyte solutions, wherein an apparatus (A) for sterilizing medical instruments and other articles includes a tray (12) with an article receiving area (14). An article to be microbially decontaminated is positioned in the receiving area (14) and a microbe blocking lid (10) is closed. A water electrolysis apparatus (30) receives water, splits the water into two separate streams that pass respectively through an anode chamber (34) and a cathode chamber (36), and exposes the streams to an electric field that results in the production of a catholyte solution for cleaning and an anolyte solution for sterilization. The anolyte and catholyte are selectively circulated through the article receiving area (14) by a pump (66) to clean and microbially decontaminate the external surfaces and internal passages of an article located therein. The anolyte or deactivated anolyte provides a sterile rinse solution Although said apparatus of WO 9908719 is extremely precise and efficient—even promoting the formation of a rinsing solution—it requires distinct anolyte and catholyte solutions, in addition to a pumping system and pipelines that are extremely complex for fast everyday use on a small scale. Thus, being costly from the viewpoint of less frequent or smaller scale uses.

The Chinese utility model patent No. CN2087077 discloses um sterilizing device, which is characterized in that it is composed of a transformer, a rectifier, a reactor and a shell. When a mains supply is connected, the transformer changes voltages and makes full-bridge rectifying. Alternating current is converted into direct current. Direct current is sent to the reactor which has sodium chloride solution. Tableware is immersed into the solution and reacts directly for sterilization. Even though the device in CN2087077 is compact, it still features drawbacks deriving from the necessity for rectifying alternating current to obtain a direct current and from the use of a solution of sodium chloride as electrolyte. As discussed above and as already known to those skilled in the art, it can promote or accelerate oxidation processes on ferrous metal utensils.

As can be inferred from the description of the prior art, the need exists for an improved electrolysis device having the following features:

a) It is compact and suitable for use in small scale;

b) It is of easy and safe handling, considering people without specific training;

c) Its manufacturing costs are low;

d) It eliminates the need for specific electrolyte solution;

e) It can be used with conventional treated water or with mineral water as an electrolyte;

f) The temperature of said water to be used as an electrolyte may be (or range) from 4° C. to 120° C.;

g) It promotes sterilization using low amperage electrical treatment (LAET), with no damage or denaturation of proteins in food; and h) It promotes sterilization using low amperage electrical treatment (LAET), without promoting or accelerating oxidation processes on ferrous metal utensils.

OBJECTS OF THE PRESENT INVENTION

Accordingly, one of the objects of the present invention is the provision of a compact device for electrolytic sterilization of food and utensils according to the features of Independent Claim 1. Further features and details thereof are represented by dependent claims from 2 through 9.

BRIEF DESCRIPTION OF FIGURES

For a better understanding and a clearer view of the object of the present invention, said invention is now described with reference to the appended claims, representing the technical effect which results from a non-limiting exemplary embodiment of the scope of the present invention, wherein, schematically:

NUMERICAL REFERENCES OF FIGURES 100 compact device for electrolytic sterilization of food and utensils;
200 container;
201 electrical insulating material film;
202 radial borderline of insulating material;
210 simple handle;
220 control handle;
221 anode connection;
222 anode wiring assembly;
223 anode terminal;
224 male connector;
225 cathode connection;
226 first cathode terminal;
227 cathode wiring assembly;
228 second cathode terminal;
240 control panel;
300 lid;
301 glass dome;
302 hand grip;
303 isolation ring;
304 flange;
305 cathode shaft;
306 cathode disc;
307 cathode wiring assembly;
308 cathode terminal;
309 cable guides;
310 insulating screen;
320 circular framing;
400 security sensor of the container;
401 security sensor of the lid;
500 fluid presence sensor;
P female plug; and
X course of the cathode disc.

DETAILED DESCRIPTION OF INVENTION

Figure 1:
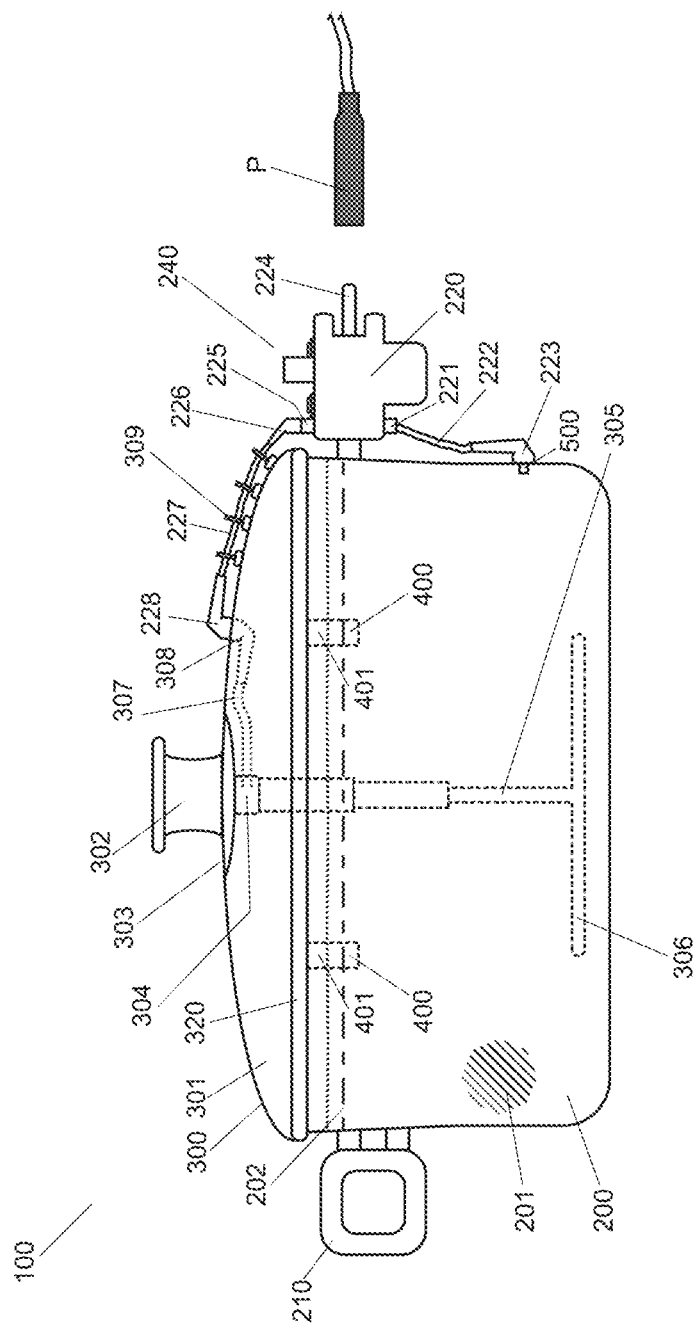
FIG. 1: exhibits a side view of a compact device for electrolytic sterilization of food and utensils according to the invention.
Figure 2:
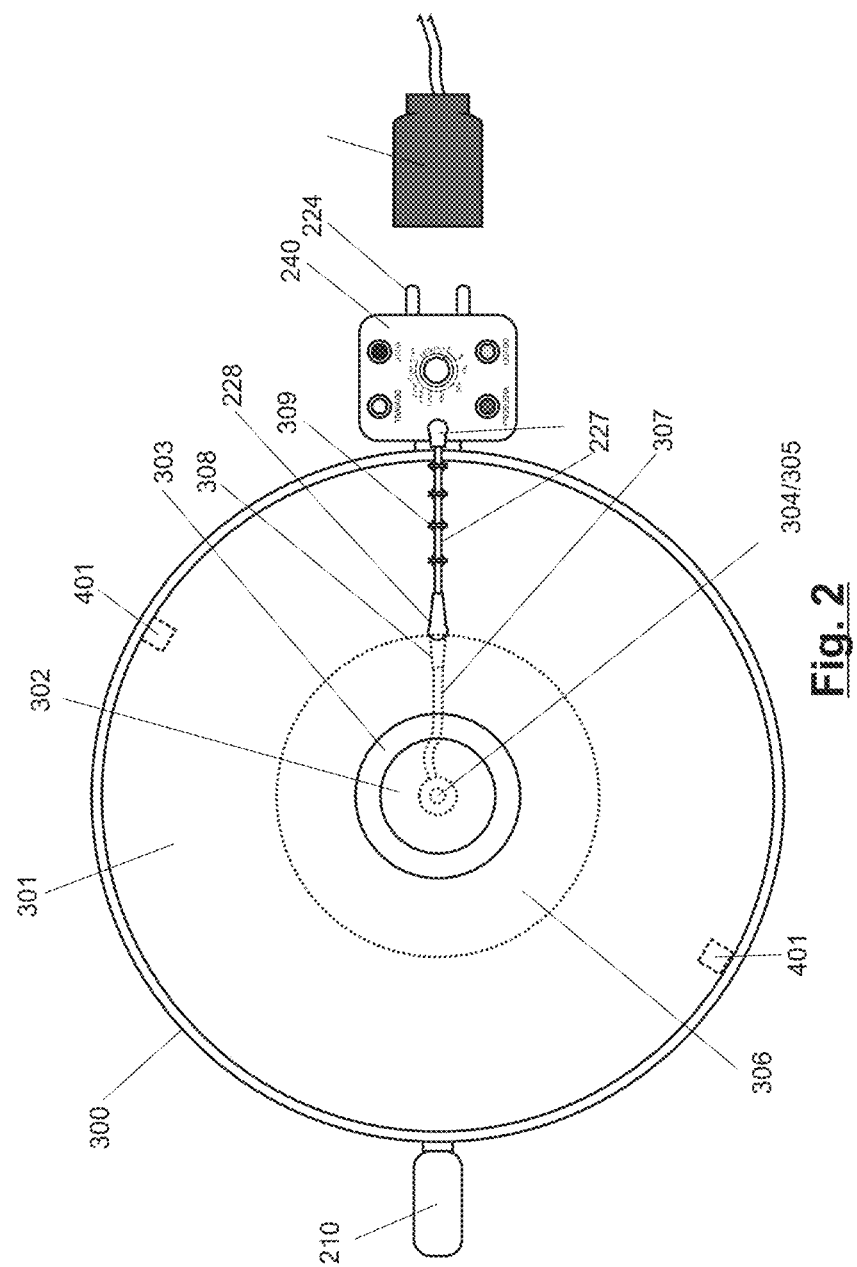
FIG. 2: exhibits a top view of a compact device for electrolytic sterilization of food and utensils according to the invention.
Figure 3:
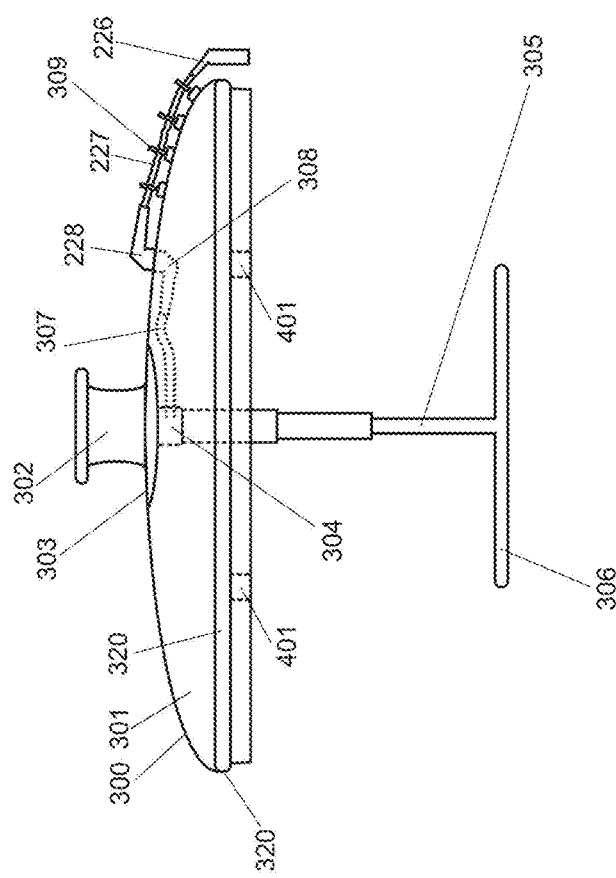
FIG. 3: exhibits a side view of the lid of a compact device for electrolytic sterilization of food and utensils according to the invention.
Figure 4:
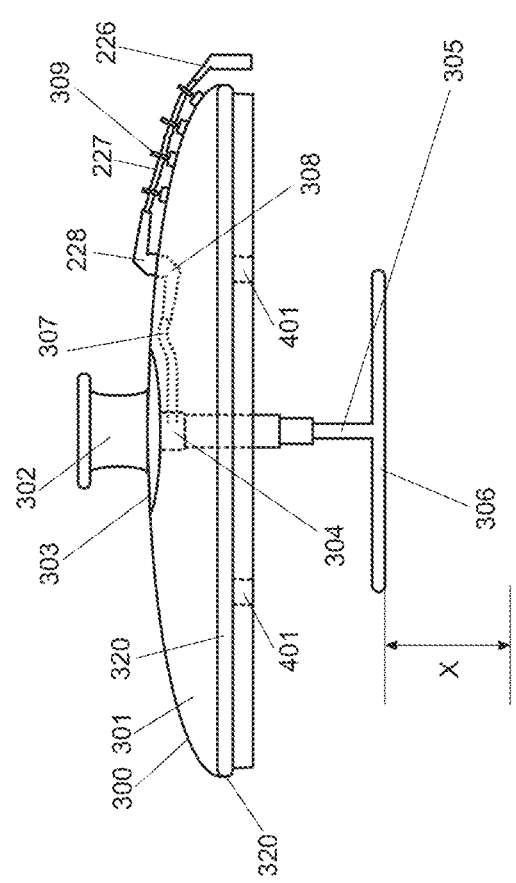
FIG. 4: exhibits a side view of the lid of a compact device for electrolytic sterilization of food and utensils according to the invention, said cathode shaft being partially retracted.
Figure 5:
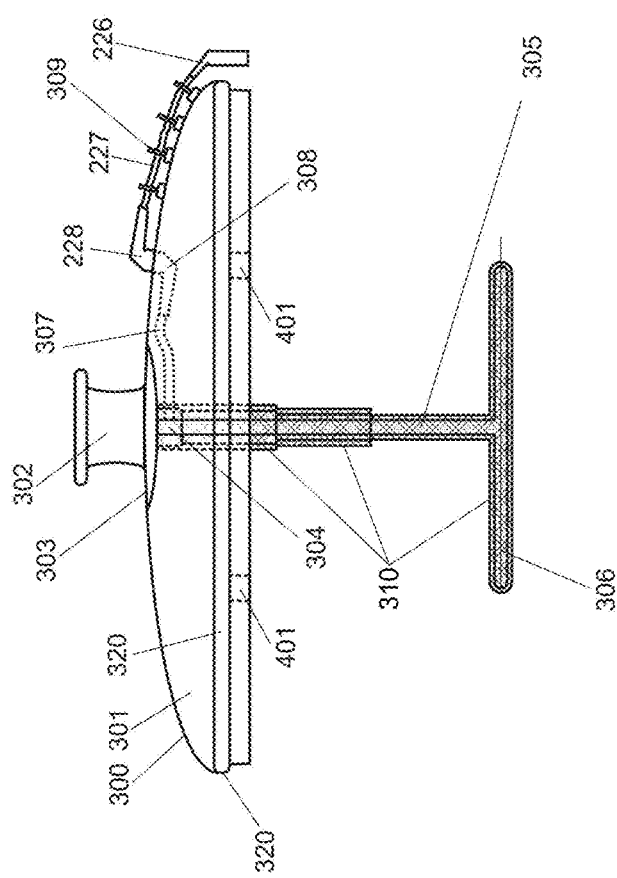
FIG. 5: exhibits a side view of the lid of FIG. 3 provided with an insulating screen.

The present invention is now described in further details based on the appended FIGS. 1, 2, 3, 4 and 5, which exhibit schematic views of said compact device for electrolytic sterilization of food and utensils 100 according to the invention, hereinafter referred to only as device 100.

As can be seen in the above mentioned FIGS. 1, 2, 3, 4 and 5, the device 100 is basically provided with a container 200 and with a lid 300.

The container 200 is provided with a simple handle 210 and with a control handle 220, and assumes the function of anode or positive pole in the electrolytic system comprised by the device 100. Said container is preferably made of stainless steel and provided with an electrical insulating material film 201 on the entirety of its outer surface. To further increase the safety of the device user, the electrical insulating material film 201, in addition to covering the outer surface of the container 200 as a whole, must extend itself over the upper edge of said container, invading the inner surface of the container 200, moving from the top down up to a radial borderline of insulating material 202, which is internal to said container 200—the height of which being from about 5% to 10% of the total height of the container 200.

Diametrically opposite to the simple handle 210 of the container 200, the control handle 220 is provided, which represents the electrical energy control and distribution unit of the present device 100.

Said control handle 220 is provided with an anode connection 221 which has an anode wiring assembly 222 connected in a fixed configuration (non-removable) thereto. Said anode wiring assembly 222 has an anode terminal 223 directly connected—again, in a fixed configuration—to the metallic part of the container 200, going through the electrical insulating material film 201 just far enough to ensure electrical contact without compromising safety.

Said control handle 220 is also provided with a cathode connection 225 which has the first cathode terminal 226 removably connected thereto. This first cathode terminal 226 has a cathode wiring assembly 227 ending on a second cathode terminal 228, removably connected to the lid 300, more specifically, to a cathode terminal 308 of the lid 300, as will be described below.

The control handle 220 has a simple electrical circuit for distribution of electricity (not shown) and the present device 100 is powered by means of the male connector 224 (having two or three pins, in accordance with the current legislation of the country of use of the device 100) to which any suitable electric extension cord can be connected, this cord being provided with a female plug P on one of its ends.

Said distribution circuit divides the input phases of electric power in order to provide a positive pole power to the container 200 by using the assembly formed by anode connection 221, anode wiring assembly 222 and anode terminal 223, and a negative pole connection to the lid 300 by using the assembly formed by cathode connection 225, first cathode terminal 226, cathode wiring assembly 227 and second cathode terminal 228, as described above.

Furthermore, the control handle 220 has a timer (not shown) to regulate the operation time and a control panel 240, which will be described in greater detail below.

The lid 300 is provided with a glass dome 301 or other suitable transparent insulating material, with a hand grip 302 disposed over an isolation ring 303, the bottom of which has a flange 304 engaged to it, to which the cathode shaft 305 is engaged too. On the opposite end to said flange 304, said cathode shaft 305 has a cathode disc 306, which must always be completely immersed in the water to be discharged within the container 100.

Said cathode shaft 305 has a telescopic configuration with a spring (not shown) inside, thus allowing for a course X of the cathode disc 306 between an extended position (see FIG. 3) and a retracted or partially retracted position (see FIG. 4), always adapting to the size of the object to be sterilized or the height of the stack of objects to be sterilized.

With respect to sterilization of metallic materials, It is important to stress that said telescopic configuration must never allow for any contact between the cathode disc 306, the metal object and the bottom of the container 200.

Furthermore, also with respect to sterilization of metallic materials, said flange 304, the cathode shaft 305 and the cathode disc 306 can be covered by a flexible insulating screen 310, which prevents direct contact of metal with said cathode elements, according to the invention.

The lid 300 is also provided with a cathode wiring assembly 307 and with a cathode terminal 308 to which, as described above, the second cathode terminal 228 is connected to in a removable fashion. Cable guides 309 ensure conduction of the cathode wiring assembly 227 between the lid 300 and the control handle 220.

All connections that are irremovable herein, essentially are so for security reasons.

All connections that are irremovable herein, are so for ease of use and, as is the case regarding the cathode connection 225, to allow for the removal of the lid 300.

The lid 300 shows a circular framing 320 made of insulating material and which extends itself into the lid 100. However, it never trespasses the radial borderline of insulating material 202 upon the closure of the lid 300 over the container 100.

It is noteworthy that said device 100 can be powered with alternating current directly from the usual electrical networks, i.e. the 127V at 60 Hz or 230V at 50 Hz or 60 Hz networks. Thus, the electric current that will flow through the device 100, more specifically the one to properly enter the device by means of the male connector 224 of the control handle 220, will be determined mainly based on the electrical resistances of the container 200, of the fluid, and of the assembly formed by flange 304, cathode shaft 305 and cathode disc 306.

However, the electric current that will flow through the liquid, if it is tap water or mineral water, depends on the distance between the cathode disc 306 and the bottom of the container 200, varying according to the course X of the cathode disc 306. That is, the current responsible for the electrolysis process will always be automatically suitable to the size of the object to be sterilized.

In order to guarantee safety for the user in all situations of using alternating current device in liquid medium, the container 200 has at least two security sensors of the container 400, disposed diametrically opposite to each other. In turn, the lid 300 has at least two security sensors of the lid 401, equally disposed diametrically opposite to each other. The device 100 is activated only if said sensors 400, 401 are axially aligned.

On the inner side of the container 200 (e.g., at the same height as said anode terminal 223) there is a fluid presence sensor 500 that only allows for the device to be activated 100 if the fluid level inside the container 200 is high enough to fully cover the fluid presence sensor 500. It is noteworthy that said fluid presence sensor 500 can be arranged in other positions, provided the guaranteed fully coverage of the cathode disc 306.

Said device 100 provides additional security since it can only be activated when said first cathode terminal 226 is connected to the cathode connection 225 and the second cathode terminal 228 is connected to the cathode terminal 308. This condition is guaranteed by a commercially available usual current sensor (not shown) arranged inside the control handle 220, which only allows for the device to be activated 100 if there is contact between the cathode terminal 308 and the cathode connection 225.

Although the present invention relates to a compact device 100, it is worth mentioning that larger devices 100 are possible. Tests were performed in devices 100 having power supply voltages in alternate current of up to 5 kV, suitably equipped with transformers. It is noteworthy that, when it coming to the use of voltages in the region of kV, it is necessary to use an electrical insulating material film (201) and insulating screen (310) made of materials that are properly adequate to said voltages.

Although the present invention relates to a device 100 powered by alternating current, tests were performed using direct current power, wherein, by means of a rectifier and a potentiometer, ionization studies were carried out, also with low electric current. From said studies, excellent results were obtained, being highly beneficial in the elimination of various carcinogenic toxins.

CONCLUSION

As can be inferred from the above description, the present invention discloses a compact device 100 for electrolytic sterilization of food and utensils capable of solving the pertinent prior art drawbacks, thus providing a device 100 which includes the following features:

a) It is compact and suitable for use in small scale;
b) It is of easy and safe handling, considering people without specific training;
c) Its manufacturing costs are low;
d) It eliminates the need for specific electrolyte solution;
e) It can be used with conventional treated water or with mineral water as an electrolyte;
f) The temperature of said water to be used as an electrolyte may be (or range) from 4° C. to 120° C.;
g) It promotes sterilization using low amperage electrical treatment (LAET), with no damage or denaturation of proteins in food; and
h) It promotes sterilization using low amperage electrical treatment (LAET), without promoting or accelerating oxidation processes on ferrous metal utensils.

FINAL CONSIDERATIONS

Those skilled in the art will easily comprehend that modifications can be made to the present invention, without departing from the above mentioned concepts. These modifications must be understood as being encompassed by the scope of the present invention. Accordingly, the particular embodiments described in further details are to be understood as being merely illustrative, and without limitative purposes, regarding the scope of the present invention. To said scope, one must grant it the entirety of the appended claims and of each and every equivalent thereof.

The invention claimed is:

1. Compact device for electrolytic sterilization of food and utensils, especially for the electrical treatment of food and utensils using the electric current generated between a positive pole and a negative pole of an electrolysis system, all of those immersed in a fluid medium contained within the device, the device comprising a container covered by a lid, wherein:
   the container is the anode or positive pole;
   the lid, by means of a spring-loaded cathode shaft provided with a cathode disc, is the cathode or negative pole;
   the electrolyte is water; and
   the device is powered by alternating current or direct current, wherein the electric current generated in the electrolyte is inversely proportional to a course of the cathode disc.

2. The device of claim 1, wherein the container is provided with an electrical insulating material film disposed on the entirety of its external surface and extending over the upper edge of said container, up to a radial borderline of insulating material of the inner surface of the container, wherein the height of said radial borderline of insulating material is from 5% to 10% of the total height of the container.

3. The device of claim 1, wherein the device is powered by alternating current.

4. The device of claim 1, wherein the container is provided with a control handle provided with an anode connection, with an anode wiring assembly, with an anode terminal, with a male connector, with a cathode connection, with a first cathode terminal, with a cathode wiring assembly, with a second cathode terminal and with a control panel.

5. The device of claim 1, wherein the lid is provided with a glass dome or other suitable transparent insulating material, with a hand grip, with an isolation ring, with a flange, with the cathode shaft, of the cathode disc, with a cathode wiring assembly, with a cathode terminal and with cable guides, with an insulating screen and with a circular framing.

6. The device of claim 1, wherein the cathode shaft is telescopic and in that it allows for the course of the cathode disc between an extended position and a retracted or partially retracted position.

7. The device of claim 1, wherein the container has at least two security sensors of the container, disposed diametrically opposite to each other and in that the lid has at least two security sensors of the lid, disposed diametrically opposite to each other, wherein the device is activated only if said sensors are axially aligned.

8. The device of claim 1, further comprising a fluid presence sensor on an inner side of the container, the fluid presence sensor only allowing activation of the device if a level of the fluid medium in the container fully covers the fluid presence sensor.

* * * * *